(12) United States Patent
Maiden

(10) Patent No.: US 8,942,449 B2
(45) Date of Patent: Jan. 27, 2015

(54) CALIBRATION OF A PROBE IN PTYCHOGRAPHY

(75) Inventor: Andrew Maiden, Sheffield (GB)

(73) Assignee: Phase Focus Limited, Sheffield (GB)

( * ) Notice: Subject to any disclaimer, the term of this patent is extended or adjusted under 35 U.S.C. 154(b) by 237 days.

(21) Appl. No.: 13/807,251

(22) PCT Filed: Jun. 27, 2011

(86) PCT No.: PCT/GB2011/051205
§ 371 (c)(1),
(2), (4) Date: May 15, 2013

(87) PCT Pub. No.: WO2012/001397
PCT Pub. Date: Jan. 5, 2012

(65) Prior Publication Data

US 2013/0223685 A1    Aug. 29, 2013

(30) Foreign Application Priority Data

Jun. 28, 2010 (GB) .................................. 1010822.3

(51) Int. Cl.
*G06K 9/00* (2006.01)
*G06K 9/32* (2006.01)
*G01N 23/205* (2006.01)
*G01T 1/29* (2006.01)

(52) U.S. Cl.
CPC ............ *G06K 9/3241* (2013.01); *G01N 23/205* (2013.01); *G01T 1/2914* (2013.01)
USPC ............................. 382/128; 382/103; 382/181

(58) Field of Classification Search
None
See application file for complete search history.

(56) References Cited

U.S. PATENT DOCUMENTS

| 5,347,375 A | * | 9/1994 | Saito et al. | ......................... 359/9 |
| 7,127,109 B1 | * | 10/2006 | Kim | ............................... 382/210 |
| 7,907,773 B2 | * | 3/2011 | Bates et al. | .................... 382/154 |

FOREIGN PATENT DOCUMENTS

| GB | 2403616 A | 1/2005 |
| WO | WO2005106531 | 11/2005 |
| WO | WO 2009/077779 | 6/2009 |
| WO | WO 2010/035033 | 4/2010 |
| WO | WO 2010/064051 | 6/2010 |

OTHER PUBLICATIONS

Maiden A.M. e. a. "An Improved Ptychographical Phase Retrieval Algorithm for Diffractive Imaging", Ultramicroscopy, Elsevier, Amstedam, N.L., vol. 109, No. 10 Sep. 1, 2009, pp. 1256-1262.
Written Opinion for PCT/GB2011/051205, dated Oct. 26, 2012, (7 pgs.).
International Search Report for PCT/GB2011/051205, dated Oct. 26, 2012, (4 pgs.).
Search Report for GB10100822.3, dated Apr. 1, 2011, (4 pgs.).
International Preliminary Report on Patentability for PCT/GB2011/051205, dated Jan. 10, 2013, (7 pgs.).

* cited by examiner

*Primary Examiner* — Manav Seth
(74) *Attorney, Agent, or Firm* — Faegre Baker Daniels LLP

(57) ABSTRACT

A method of providing image data for constructing an image of a region of a target object, comprising providing a reference diffraction pattern of a reference target object; determining an initial guess for a probe function based upon the reference diffraction pattern; and determining, by an iterative process based on the initial guess for the probe function and an initial guess for an object function, image data for a target object responsive to an intensity of radiation detected by at least one detector.

20 Claims, 3 Drawing Sheets

CALIBRATION OF A PROBE IN PTYCHOGRAPHY

Cross Reference to Related Application

This application is a U.S. national stage patent application of PCT/GB2011/051205, filed Jun. 27, 2011, which claims priority to Great Britian Application No. 1010822.3 filed Jun. 28, 2010, the entire disclosures of each are hereby expressly incorporated by reference herein.

The present invention relates to a method and apparatus for providing image data of the type which may be utilised to construct an image of a region of a target object. In particular, but not exclusively, the present invention relates to a method of providing such image data using an iterative process making use of an unknown probe function.

BACKGROUND

Many types of imaging techniques are known for deriving spatial information about a target object (sometimes referred to as a specimen). However, it is often not possible to directly image a target specimen by conventional means such as brightfield microscopy. For example in conventional transmission imaging an object is irradiated by plane wave illumination. The waves scattered by the object are re-interfered by a lens to form an image. In the case of very short wave length imaging (X-rays or electrons) this technique has many known difficulties associated with aberrations and instabilities introduced by the lens which limit the resolution and interpretability of the resulting image. Typical achievable resolution is many times larger than the theoretical limit. Other types of imaging techniques are known but many of these have problems such as resolution limits, long data gathering times or the need for complex and expensive equipment.

In many instances it is possible to derive some of the properties of the specimen by measuring the way in which it scatters incident radiation. The distribution of scattered radiation at some distance from a specimen is known as a diffraction pattern and if the radiation is sufficiently coherent, it is possible to form an image of the specimen from measurement of its diffraction pattern. One technique for forming this image is named ptychography. Here, a target specimen is illuminated by a sufficiently coherent wave-front, known as the 'probe', whose intensity is concentrated within a localised lateral region where it interacts with the specimen. A set of diffraction patterns is then recorded by one or more detectors, with each pattern corresponding to a different relative lateral position of the specimen and probe. These positions are chosen such that an area of interest of the specimen is covered by multiple overlapping positions of the probe. An example of this technique for high resolution imaging has been disclosed in WO 2005/106531, which is herein incorporated by reference for all purposes. The technique disclosed in WO 2005/106531 is now referred to by those skilled in the art as the ptychographical iterative engine (or PIE). This involves providing incident radiation from a radiation source at a target object; detecting, via at least one detector, the intensity of radiation scattered by the target object and providing image data responsive to the detected intensity without high resolution positioning of the incident radiation or a post target object aperture relative to the target object; and using the detected intensity to produce image data for constructing an image of a region of a target object. The image data may be produced using an iterative process using a moveable softly varying probe function such as a transmittance function or illumination function.

PIE provides a powerful technique for the recovery of image data relating to an area of an object from a set of diffraction pattern measurements. Each diffraction pattern is formed by illuminating an object with a known wave front of coherent radiation with the requirement that the intensity of the wave front is concentrated within a localised lateral region where it interacts with the object. Examples of such a wave front would be that generated a short distance beyond an aperture when it is illuminated by a plane wave, or the focal spot generated by a convex lens illuminated by a plane wave. The technique is also applicable to scenarios where a target is illuminated by plane wave radiation and a post target object aperture is used to select illumination scattered by a region of the object.

In this sense a diffraction pattern is the distribution of intensity produced by an optical configuration some distance beyond the object and at a plane normal to the direction of propagation of the illumination wave front. This plane is designated as the measurement plane and measurements made at this plane are denoted $\psi k$ (u) with u being an appropriate coordinate vector. It is to be noted that when the distance between the measurement plane and a sample plane is small the diffraction pattern is known as a near-field diffraction pattern. When this distance is large the diffraction pattern is known as a far-field diffraction pattern.

Ptychography makes use of several diffraction patterns recorded at the measurement plane using a suitable recording device such as a CCD camera or the like. The lateral positions of the object and the localised illumination wave front are different for each pattern.

A limitation of PIE is the requirement that, in order to provide useful image data, characteristics of a probe function (e.g. a transmittance function associated with a post target object aperture or an illumination function associated with incident radiation) must be known or estimated. This requires time consuming set up techniques and can lead to inaccuracies if the probe function used is inaccurate.

This limitation of PIE may be addressed by a technique disclosed in WO2010/064051, which is herein incorporated by reference for all purposes. The technique described in WO2010/064051 is referred to as extended Ptychographical Iterative Engine, or ePIE. This technique begins with a rough initial estimate of the probe wave-front and a rough initial estimate of the target specimen. Each iteration of the ePIE produces updated estimates of the probe and of the specimen. The initial estimates need not be accurate; it is possible for the algorithm to produce an image given only a rough initial guess at the probe's shape. However, it is possible that the algorithm will fail to produce an accurate image. In some cases each iteration of the ePIE will produce estimates of the specimen and of the probe that are less accurate than those resulting from the previous iteration, and the algorithm is said to diverge.

It is an aim of the present invention to at least partly mitigate the above-mentioned problems.

Ptychography is applicable to imaging performed in either the reflection mode (where the illuminating beam is reflected from the target specimen) or the transmission mode (where the illuminating beam is transmitted through the target specimen.) Herein, when transmission/transmissive/transmit is used it should be understood that reflection/reflective/reflect could equally well be used.

BRIEF SUMMARY OF THE DISCLOSURE

In accordance with the present invention there is provided a method of providing image data for constructing an image of a region of a target object, comprising: providing a reference diffraction pattern of a reference target object; determining an initial guess for a probe function based upon the reference diffraction pattern; and determining, by an iterative process based on the initial guess for the probe function and an initial guess for an object function, image data for a target object responsive to an intensity of radiation detected by at least one detector.

The reference diffraction pattern may be based on an intensity of radiation detected by the at least one detector.

The radiation detected by the at least one detector may be reflected from the reference target object, or may be transmitted through the reference target object.

The initial guess for the probe function may be used to determine image data for one or a plurality of target objects.

The reference target object may be a first target object for which image data is determined.

The reference target object may be a target object only used for calibration purposes.

Determining an initial guess for a probe function may comprise: estimating, based on the reference diffraction pattern, a power of radiation incident on a probe area of the reference target object, and selecting the initial guess for the probe function such that the initial guess for the probe function has an average intensity equal to the estimated average intensity.

Estimating an average intensity may comprise: performing a fast Fourier transform on the reference diffraction pattern to produce a matrix of complex numbers, and summing the absolute values of the complex numbers to produce a real number, wherein selecting the initial guess for the probe function comprises: taking the square-root of the real number to produce a real-valued number, N, selecting the initial guess for the probe function, P, to be P=MN/K, where M is a matrix representing the probe area, and K is a normalization factor.

K may be the sum of values in matrix M.

An estimate of the probe area may be provided, wherein values in matrix M are zero outside of the estimated probe area and are 1 inside the estimated probe area, and K is equal to the number of 1 values in matrix M.

An aspect of the invention provides a machine-readable data storage medium comprising computer executable instructions which, when executed by a computer, perform the above method.

Embodiments of the invention may be applied to improve performance of ePIE methods and systems by providing a reduction or elimination of the likelihood of divergence during the iterative refinement of the probe function.

BRIEF DESCRIPTION OF THE DRAWINGS

Embodiments of the present invention will now be described hereinafter, by way of example only, with reference to the accompanying drawings in which.

DETAILED DESCRIPTION

Figure 1:
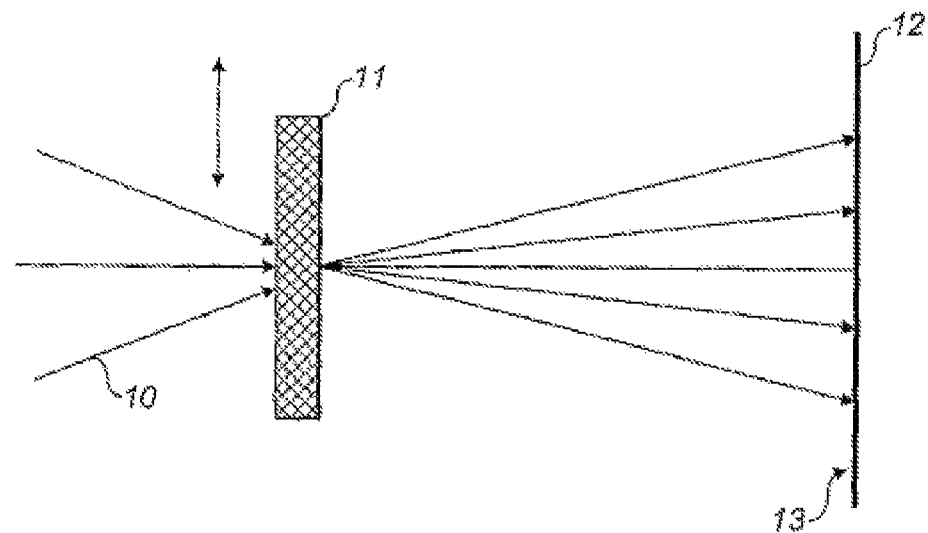
FIG. 1 illustrates incident at a target object.

In the drawings like reference numerals refer to like parts.

FIG. 1 illustrates how a scattering pattern may be developed and used to determine image data corresponding to information about the structure of a target object. It will be understood that the term target object refers to any specimen or item placed in the path of incident radiation which causes scattering of that radiation. It will be understood that the target object should be at least partially transparent to incident radiation. The target object may or may not have some repetitive structure. Alternatively the target object may be wholly or partially reflective in which case a scattering pattern is measured based on reflected radiation.

Incident radiation 10 is caused to fall upon the target object 11. It is to be understood that the term radiation is to be broadly construed as energy from a radiation source. This will include electro magnetic radiation including X-rays, emitted particles such as electrons and/or acoustic waves. Such radiation may be represented by a wave function $\Psi(r)$. This wave function includes a real part and an imaginary part as will be understood by those skilled in the art. This may be represented by the wave functions modulus and phase. $\Psi(r)^*$ is the complex conjugate of $\Psi(r)$ and $\Psi(r)\Psi(r)^*=|\Psi(r)|^2$ where $|\Psi(r)|^2$ is an intensity which may be measured for the wave function.

The incident radiation 10 is scattered as it passes through and beyond the specimen 11. As such the wave function of the incident radiation as it exits the specimen will be modified in both amplitude and phase with respect to the wave function of the incident radiation at the pre-target side of the specimen. The scattering which occurs may include Fourier diffraction, refraction and/or Fresnel diffraction and any other form of scattering in which characteristics of the incident radiation are modified as a result of propagating after the specimen. If an array of detectors such as a CCD detector 12 is arranged a long distance from the specimen then a diffraction pattern is formed at a diffraction plane 13. A Fourier diffraction pattern will form if the detectors 12 are located a distance D from the specimen where D is sufficiently long for the diffraction pattern to be formed effectively from a point source. If the diffraction plane is formed closer to the specimen, by locating the detectors nearer, then a Fresnel diffraction pattern will be formed.

The incident radiation 10 falls upon a first surface of a target object 11. The incident radiation is scattered in the specimen and transmitted radiation propagates through to a diffraction plane 13 where a diffraction pattern forms.

Figure 2:
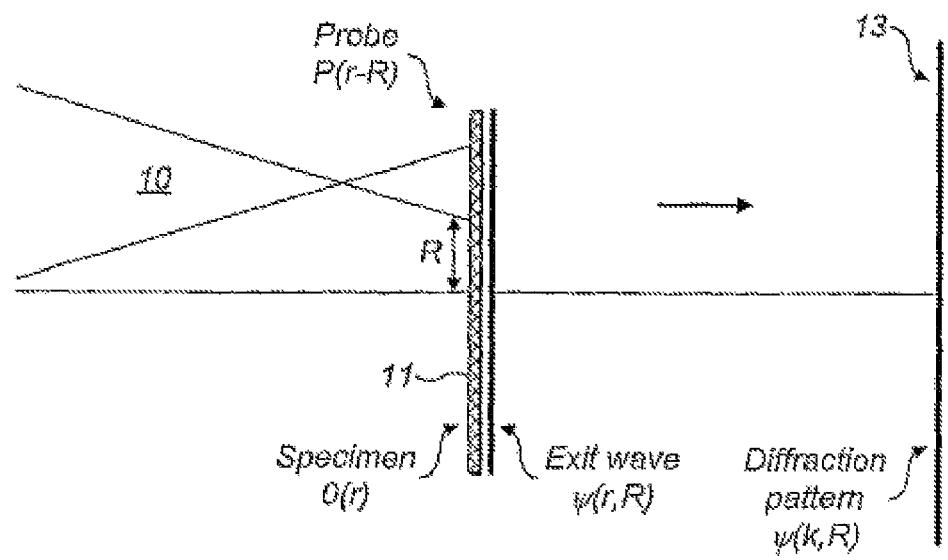
FIG. 2 illustrates a Probe Function and formation of a diffraction pattern with a target object.

FIG. 2 illustrates the process of FIG. 1 in more detail. The radiation 10 is roughly focused, for example by a weak lens, so that a region of a first surface of the target object is illuminated. The weak lens may of course comprise any appropriate focusing apparatus such as a set of plates and a voltage supply for a beam of electrons or a reflective surface for X-rays. The weak focusing is sufficient to substantially confine the probing radiation beam. It is thus not necessary to sharply focus radiation although of course strongly focussed radiation could be used. Here the target object provides an object function O(r) which represents the phase and amplitude alteration introduced into an incident wave as a result of passing through the object of interest. The illuminating radiation incident on the target object represents a probe function P(r) which forms an illumination function such as that generated by a caustic or illumination profile formed by the lens or other optical component. P(r) is the complex stationary value of this wave field calculated at the plane of the object. The exit wave function $\psi(r,R)$ defines the scattered radiation as it exits the downstream surface of the target object. As this exit wave propagates through space it will form a diffraction pattern ψ(u) at the diffraction plane 13.

It will be understood that rather than weakly (or indeed strongly) focusing illumination on a target, unfocused radiation can be used with a post target aperture. An aperture is located post target object to thereby select a region of the target for investigation. The aperture is formed in a mask so that the aperture defines a "support". A support is an area of a function where that function is not zero. In other words outside the support the function is zero. Outside the support the mask blocks the transmittance of radiation. The term aperture describes a localised transmission function of radiation. This may be represented by a complex variable in two dimensions having a modulus value between 0 and 1. An example is a mask having a physical aperture region of varying transmittance.

Incident radiation would thus fall upon the up-stream side of the specimen and be scattered by the specimen as it is transmitted. A specimen wave O(r) is thus formed as an exit wave function of radiation after interaction with the object. In this way O(r) represents a two-dimensional complex function so that each point in O(r), where r is a two-dimensional coordinate, has associated with it a complex number. O(r) will physically represent an exit wave that would emanate from the object which is illuminated by a plane wave. For example, in the case of electron scattering, O(r) would represent the phase and amplitude alteration introduced into an incident wave as a result of passing through the object of interest. The aperture provides a probe function P(r) (or transmission function) which selects a part of the object exit wave function for analysis. It will be understood that rather than selecting an aperture a transmission grating or other such filtering function may be located downstream of the object function. The probe function P(r-R) is an aperture transmission function where an aperture is at a position R. The probe function can be represented as a complex function with its complex value given by a modulus and phase which represent the modulus and phase alterations introduced by the probe into a perfect plane wave incident upon it.

The exit wave function ψ(r,R) is an exit wave function of radiation as it exits the aperture. This exit wave ψ(r,R) forms a diffraction pattern Ψ(u) at a diffraction plane. Here r is a vector coordinate in real space and u is a vector coordinate in diffraction space.

It will be understood that with both the aperture formed embodiment and the non-aperture embodiment described with respect to FIGS. 1 and 2 if the diffraction plane at which scattered radiation is detected is moved nearer to the specimen then Fresnel diffraction patterns will be detected rather than Fourier diffraction patterns. In such a case the propagation function from the exit wave ψ(r,R) to the diffraction pattern Ψ(u) will be a Fresnel transform rather than a Fourier transform.

Figure 3:
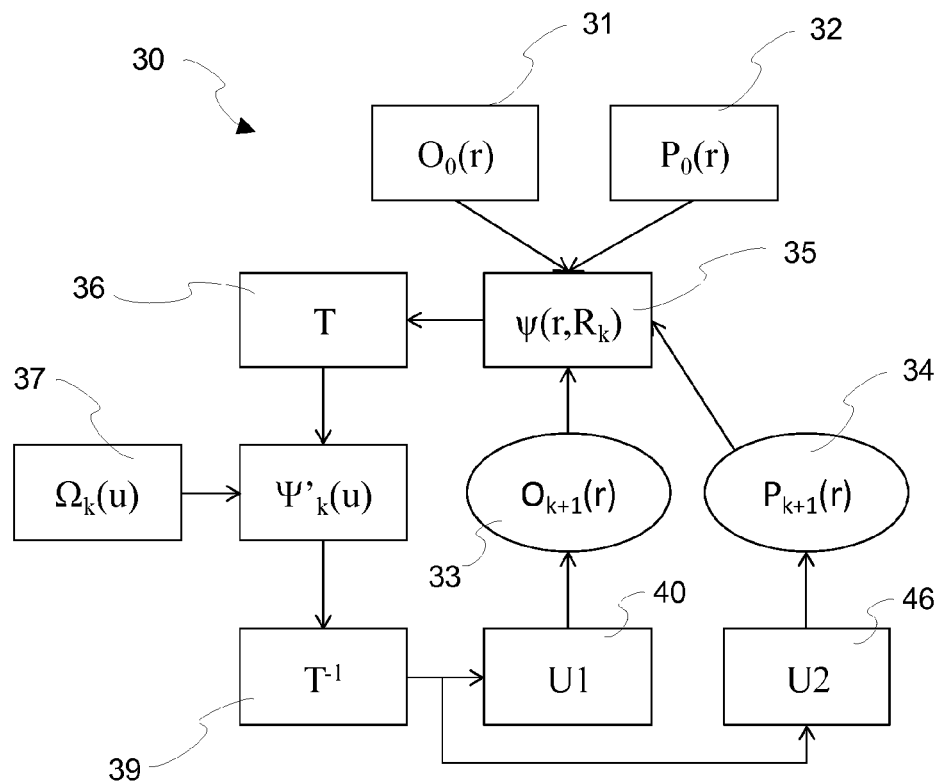
FIG. 3 illustrates a phase retrieval algorithm.

FIG. 3 illustrates an iterative process according to an embodiment of the present invention which can be used to recover image data of the type which can be used to construct an image of an area of an object from a set of diffraction patterns. The iterative process 30 illustrated begins with a guess 31 at the object and a guess 32 at the form of a probe function used. Subsequently these initial guesses are replaced by running guesses in the iterative process. The initial guesses for the image function can be a random distribution or can be a precalculated approximation based on other measurements or prior calculations. The initial guess for the probe function is described in more detail below. The guesses are modelled at a number of sample points and are thus represented by matrices. Such matrices can be stored and manipulated by a computer or other such processing unit. Aptly the sample points are equally spaced and form a rectangular array. The probe function estimation after k iterations is denoted by $P_k(r)$ and the recovered image after k iterations by $O_k(r)$. The original guesses for the probe function and objection function are thus $P_0(r)$ and $O_0(r)$ respectively where r is an appropriate coordinate vector.

If the current translation vector relating to the relative positions of the object and the probe function is denoted $R_k$ then the interaction between the guessed-at object distribution and the probe function is modelled by $$\psi_k(r,R_k) = )_k(r)P_k(r-R_k) \qquad 1$$

This is the current exit wave front. According to embodiments of the present invention an iterative process is used to update the object guess 33. An updated probe function guess 34 is also iteratively calculated.

Referring to the update of the object guess a first step is to determine the exit wave front $\psi(r, R_k)$ at step 35. This is carried out using equation 1 noted above. A next step is to propagate the exit wave front to the measurement plane which is accomplished using a suitable model of propagation for the coherent wave front. The propagation is represented by the operator T where:

$$\Psi_k(u) = T[\psi_k(r, R_k)] \qquad 2$$

The forward transform T shown as step 36 generates a propagated wave front $\Psi_k(u)$ where u references coordinates in the measurement plane. Since $\Psi_k(u)$ is complex-value this can be written as:

$$\Psi_k(u) = A_k(u)\exp(i\theta_k(u)) \qquad 3$$

Next this modelled wave front must be compared to a measured diffraction pattern. If the guessed-at object is correct then the following equality holds for every value of k.

$$A_k(u) = \sqrt{\Omega_k(u)} \qquad 4$$

The modulus of the propagated exit wave front equals the square root of the recorded diffraction pattern intensity. Generally this will not be the case as the guessed-at object will not correctly represent the true object at the sample points. To enforce the equality the modulus of the propagated exit wave front is replaced by the square root of the recorded diffraction pattern intensity as:

$$\Psi'_k(u) = \sqrt{\Omega_k(u)}\exp(i\theta_k(u)) \qquad 5$$

At step 37 the modulus of the propagated exit wave front is replaced by the square root of the recorded diffraction pattern intensity.

The corrected wave front is then propagated back to the plane of the object using the inverse propagation operator:

$$\psi'_k(r, R_k) = T^{-1}[\Psi'_k(u)] \qquad 6$$

This inverse propagation step 39 provides the corrected exit wave form $\psi'_k(r, R_k)$. An update step 40 is then calculated to produce an improved object guess $O_{k+1}(r)$. The update step 40 is carried out according to:

$$O_{k+1}(r) = O_k(r) + \alpha \frac{P_k^*(r - R_k)}{|P_k(r - R_k)|_{max}^2}(\psi'_k(r, R_k) - \psi_k(r, R_k)) \qquad 7$$

This update function is labelled U1 in FIG. 3 which generates the update of the object guess $O_{k+1}(r)$. The parameter a governs the rate of change of the object guess. This value should be adjusted between 0 and 2 as higher values may lead to instability in the updated object guess. According to embodiments of the present invention the probe function is reconstructed in much the same manner as the object function. Aptly the probe function guess is carried out concurrently with the update of the object guess. (It will be appreciated that the Probe Function could optionally be updated more often or less often than the Object Function). In order to achieve this, a further diffraction pattern, acting as a calibration diffraction pattern, may be recorded in the measurement plane with the target object removed from the system. This calibration diffraction pattern may be recorded prior to the target object being put in place or subsequent to removal of the target object after the previously mentioned diffraction patterns have been measured, or may be a combination of diffraction patterns recorded before and after the target object is duly located. Alternatively, the calibration diffraction pattern may be recorded in the measurement plane with a calibration object 511 in place of the target object. Again. this calibration diffraction pattern may be recorded prior to the target object being put in place or subsequent to removal of the target object after the previously mentioned diffraction patterns have been measured, or may be a combination of diffraction patterns recorded before and after the target object is duly located. The calibration object 511 is an object with a known object function, such that the probe function may be derived from the measured diffraction pattern and the object function.

Figure 4:
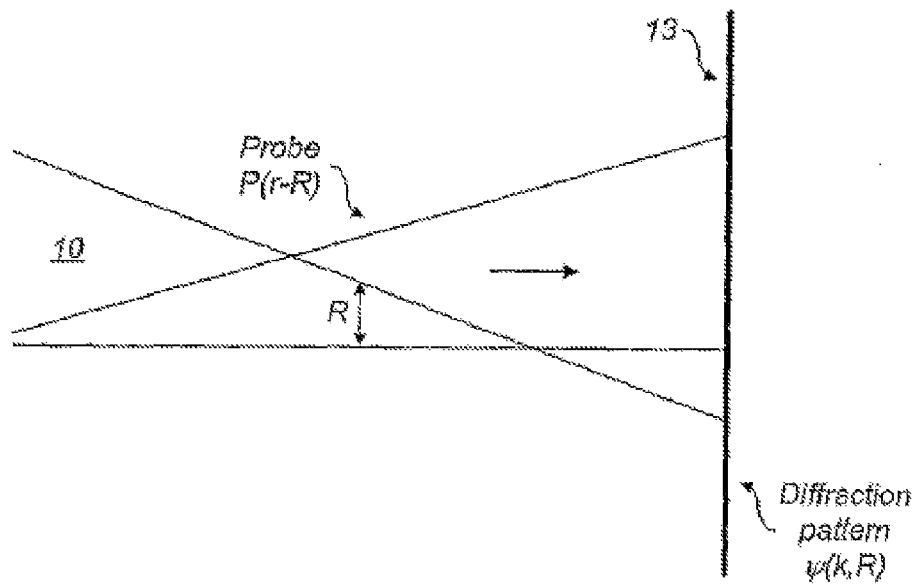
FIG. 4 illustrates a Probe Function and formation of a diffraction pattern without a target object.
Figure 5:
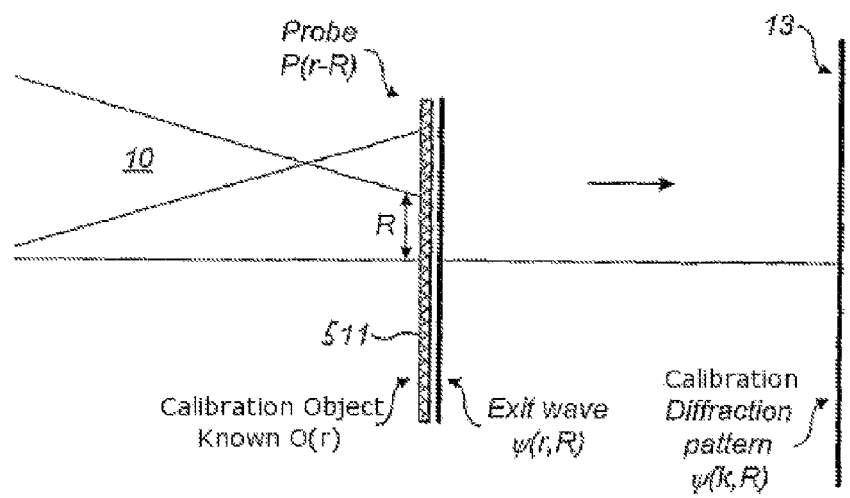
FIG. 5 illustrates a Probe Function and formation of a diffraction pattern with a calibration object.

That is to say a calibration diffraction pattern of the probe function itself may be recorded in the absence of a target object. The measurement of this diffraction pattern is illustrated in FIG. 4. An alternative arrangement is shown in FIG. 5, in which the calibration diffraction pattern is measured using a calibration object 511, having a known object function, in place of the target object. The calibration diffraction pattern is denoted as the measurement $\Omega_P(U)$.

At step 32 $P_0(r)$ is chosen as an initial guess at the probe function, as described in more detail below. Proceeding in a similar manner to the correction/update steps detailed above an update step 46 makes use of an update function U2 which is:

$$P_{k+1}(r-R_k) = P_k(r-R_k) + \beta \frac{O_k^*(r)}{|O_k(r)|^2_{max}} (\psi_k'(r, R_k) - \psi_k(r, R_k)) \quad 8$$

The result of this update function generates the running estimate for the probe function. The parameter β governs the rate of change of the probe guess. This value should be adjusted between 0 and 2 as higher values may lead to instability in the updated probe guess. The running guess for the probe function may be used at step 35 for generating the exit wave front.

An alternative iterative method to that of FIG. 3 that may be used in some embodiments is described in WO 2010/064051.

As noted above, in some cases the algorithm fails to produce an accurate image due to divergence of the algorithm. The inventors have discovered that divergence may occur when the intensity of the probe wave-front is not incorporated accurately into its initial estimate. If the modelled (guessed) intensity is too large or too small, each iteration of the ePIE will produce estimates of the specimen and of the probe that are less accurate than those resulting from the previous iteration, and the algorithm diverges.

According to embodiments of the present invention, this divergence is avoided or made less likely by providing the ePIE with an initial estimate of the probe's intensity that uses a reference diffraction pattern measured using a reference specimen. This diffraction pattern may be recorded in the same manner as those measured from the target specimen and indeed one of these patterns may in some embodiments be used as the reference diffraction pattern. When it is the radiation reflected from the reference specimen that is measured it is preferable that the reference diffraction pattern be from an area of the specimen that reflects a high proportion of the incident probe's intensity. When the measured quantity is the radiation transmitted through the reference specimen it is preferable that the reference pattern be from an area that transmits most of the incident probe's intensity. This ensures that the intensity of the reference diffraction pattern is approximately equal to the intensity of the probe. The selection of reference specimen is not particularly limited, and as noted above may be a target specimen. Alternatively, where a calibration object 511 is used to determine the calibration diffraction pattern, the calibration diffraction pattern may be used as the reference diffraction pattern.

The measured diffraction pattern is used to calculate the power of the radiation incident on the specimen in the area of the probe. This calculated power can then be used, along with an approximate knowledge of the area of the probe, to derive an averaged intensity, or alternatively an averaged amplitude, of the incident radiation across the area of the probe. Here, the term area of the probe is used it signify the area of the specimen that gives rise to the measured diffraction pattern.

According to an example of this embodiment, the initial probe is formed by performing a Fast Fourier Transform (FFT) on the reference diffraction pattern (e.g. the intensity measured using a reference specimen). This results in a matrix of complex numbers, whose absolute values are next summed to give a value representative of the power of the radiation incident in the area of the probe. The square-root of this sum is then taken to give a single real-valued number N representative the RMS amplitude of the radiation integrated over the area of the probe. An estimate is now made of the area outside of which the true probe falls to a low level of intensity, to give the rough shape of the probe. This is represented in a computer by a matrix M whose values are zero (0) where the probe is thought to be below the threshold intensity and one (1) where it is thought to be above the threshold. The total number of 1's in M is calculated to give a real-valued number K. The initial probe estimate is then represented in the computer by the matrix P, where:

$$P = MN/K \quad 9$$

That is, each entry in the matrix M is multiplied by N and divided by K. This results in an initial guess for the probe function that has approximately the same amplitude, and so the same intensity, as the incident radiation averaged across the area of the probe. The initial guess for the probe function is zero outside the approximate area of the probe and has a constant, uniform value within the area of the probe.

As would be clear to the skilled person, some or all of the above mathematical operations above may be performed using a computer.

According to these embodiments, the likelihood of divergence during the iterative refinement of the probe function is reduced or eliminated by providing an initial guess for the probe function that has a suitable intensity, by selecting the intensity of the guessed probe function to be an average estimated intensity, based on a measured reference diffraction pattern.

In some preferred embodiments, the estimate of the probe's intensity may be used in multiple iterative algorithmic processes from multiple target specimens. That is, it may not be necessary to collect the initial estimate of the probe's intensity for every target specimen investigated.

Figure 6:
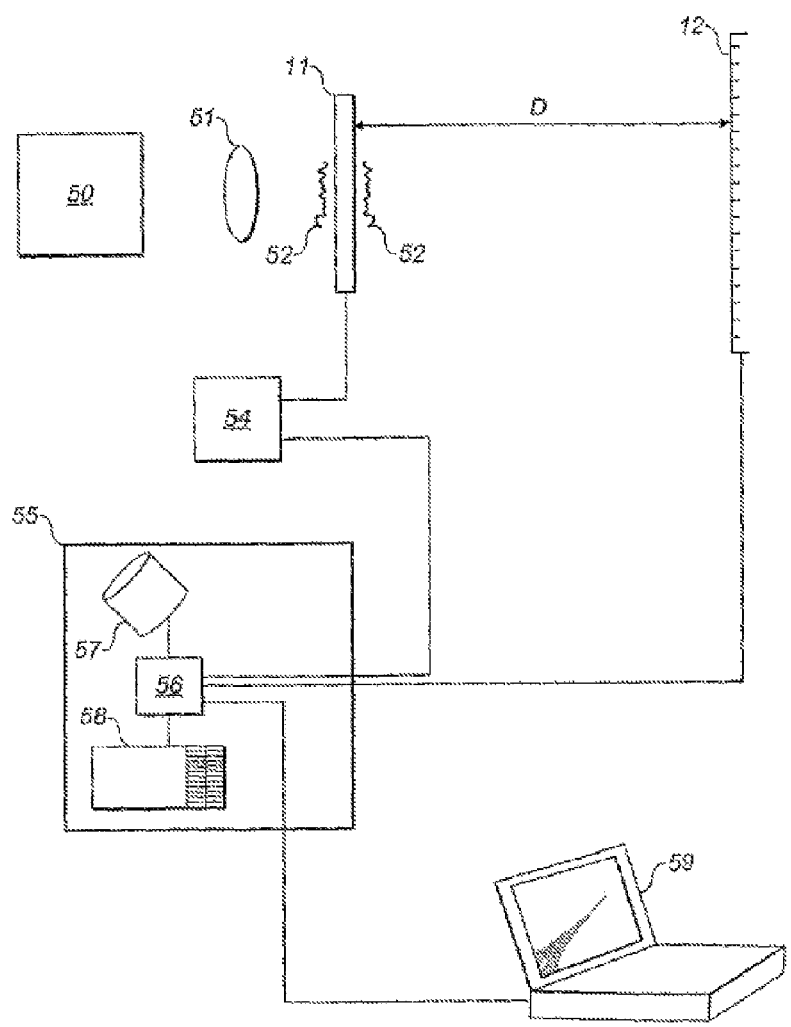
FIG. 6 illustrates apparatus for providing image data which may be used to construct a high-resolution image of a region of a target object.

FIG. 6 illustrates apparatus for providing image data which may be used to construct a high-resolution image of a region of a target object according to the above-described embodiment illustrated in FIGS. 1 and 2. A source of radiation 50 provides illumination onto a lens 51 which weakly focuses the radiation onto a selected region of a target 11. The incident radiation has an incident wave function 52 and an exit wave function 53. This exit wave function is propagated across distance D where a diffraction pattern is formed on an array of detectors 12. The distance D is advantageously sufficiently long so that the propagated exit wave function 53 forms a Fourier diffraction pattern in the far-field. The detector array provides at least one detector which can detect the intensity of radiation scattered by the target object 11. A locating device 54 is provided which may be a micro actuator and this can locate the target object at one or more locations as desired with respect to the target object. In this way radiation from source 50 may be made incident on different locations of the upstream surface of the target 11.

Alternatively, in some applications it may be advantageous for the distance D to be sufficiently small so that the propagated exit wave function 53 forms a Fresnel diffraction pattern on the detector array in the near field.

A control unit 55 provides control signals to the micro actuator and also receives intensity measurement results from each of the pixel detectors in the detector array 12. The control unit 55 includes a microprocessor 56 and a data store 57 together with a user interface 58 which may include a user display and a user input key pad. The control unit may be connected to a further processing device such as a laptop 59 or PC for remote control. Alternatively it will be understood that the control unit 55 could be provided by a laptop or PC. The control unit 55 can automatically control the production of image data in real time. Alternatively a user can use the user interface 58 to select areas of the target object for imaging or provide further user input.

In use the source of radiation 50 illuminates the lens 51 with radiation. The target object 11 is selectively located by the actuator 54 under control of the control unit 55. The radiation forms a diffraction pattern detected at respective locations by each of the detectors in the detector array 12. Results from these detectors is input to the control unit and may be stored in the data store 57. If only one position is being used to derive image data the microprocessor uses this detected information together with program instructions including information about the algorithm above-noted to derive the image data. However if one or more further positions are required prior to finalising the image data the control unit next issues signals to the actuator 54 which locates the specimen at another selected location. The actuator may place the specimen at one of many different positions. After relocation a further diffraction pattern formed on the detector array is measured and the results stored in the control unit. As an example the array 12 may be a CCD array of 1200×1200 pixels. If no further intensity measurements are required image data may at this stage be generated by the control unit in accordance with the two newly stored sets of results using the algorithm above-noted. The raw image data may be displayed or a high-resolution image generated from the image data may be displayed on the user interface 1209 or remote display on a PC or other such device. Alternatively or additionally the image data itself may be utilised to determine characteristics associated with the target object (for example by data values being compared with predetermined values.

The actuator can be used to move the target object out of the optical path to enable the diffraction pattern without target object to be measured. Alternatively this movement may be effected by another actuator (not shown) or by user interference.

According to a further embodiment of the invention, a diffuser covers a post-target aperture. The diffuser is arranged to diffuse the wavefront from the target such that the radiation incident on the sample is spread more evenly over all diffraction angles in the measured diffraction pattern. By performing the measurements required to recover the illumination function, or probe function, with the diffuser in place, the effect of the diffuser can be automatically recovered as well. Thus, the diffuser may diffuse the wavefront from the target in an arbitrary way, and it is not necessary to know a priori the nature of the diffuser.

The presence of the diffuser leads to a reduction in the dynamic range of the diffraction pattern. As most detectors have limited dynamic range, reducing the dynamic range of the diffraction pattern may allow a more faithful representation of the diffraction pattern to be determined. Furthermore, as the radiation incident on the sample is spread more evenly over all diffraction angles, the incident flux required to provide the image data may be reduced, thereby reducing the possibility of causing damage to the target object.

Any type of diffuser having an arbitrary transfer function may be used. As will be understood by the skilled man, the choice of diffuser will depend on the properties of the radiation used, and the desired diffusion effect. For example, for visible light the diffuser may comprise a ground glass diffuser.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method of providing image data for constructing an image of a region of a target object, comprising:
   providing a reference diffraction pattern of a reference target object;
   determining an initial guess for a probe function based upon the reference diffraction pattern; and
   determining, by an iterative process based on the initial guess for the probe function and an initial guess for an object function, image data for a target object responsive to an intensity of radiation detected by at least one detector.

2. The method of claim 1 wherein the reference diffraction pattern is based on an intensity of radiation detected by the at least one detector.

3. The method of claim 1 wherein the radiation detected by the at least one detector is reflected from the reference target object.

4. The method of claim 1 wherein the radiation detected by the at least one detector is transmitted through the reference target object.

5. The method of claim 1 wherein the initial guess for the probe function is used to determine image data for one or a plurality of target objects.

6. The method of claim 1 wherein the reference target object is a first target object for which image data is determined.

7. The method of claim 1 wherein the reference target object is a target object only used for calibration purposes.

8. The method of claim 1 wherein determining an initial guess for a probe function comprises:
   estimating, based on the reference diffraction pattern, a power of radiation incident on a probe area of the reference target object, and
   selecting the initial guess for the probe function such that the initial guess for the probe function has an average intensity equal to the estimated average intensity.

9. The method of claim 8, wherein estimating an average intensity comprises:
   performing a fast Fourier transform on the reference diffraction pattern to produce a matrix of complex numbers, and
   summing the absolute values of the complex numbers to produce a real number, and wherein
   selecting the initial guess for the probe function comprises:
      taking the square-root of the real number to produce a real-valued number, N,
      selecting the initial guess for the probe function, P, to be P=MN/K, where
      M is a matrix representing the probe area, and K is a normalization factor.

10. The method of claim 9, wherein K is the sum of values in matrix M.

11. The method of claim 9, further comprising providing an estimate of the probe area, wherein
   values in matrix M are zero outside of the estimated probe area and are 1 inside the estimated probe area, and
   K is equal to the number of 1 values in matrix M.

12. A non-transitory machine-readable data storage medium comprising computer executable instructions which, when executed by a computer, perform the method according to claim 1.

13. The method of claim 2 wherein determining an initial guess for a probe function comprises:
   estimating, based on the reference diffraction pattern, a power of radiation incident on a probe area of the reference target object, and
   selecting the initial guess for the probe function such that the initial guess for the probe function has an average intensity equal to the estimated average intensity.

14. The method of claim 13, wherein estimating an average intensity comprises:
   performing a fast Fourier transform on the reference diffraction pattern to produce a matrix of complex numbers, and
   summing the absolute values of the complex numbers to produce a real number, and wherein
   selecting the initial guess for the probe function comprises:
      taking the square-root of the real number to produce a real-valued number, N,
      selecting the initial guess for the probe function, P, to be P=MN/K where
      M is a matrix representing the probe area, and K is a normalization factor.

15. The method of claim 13, further comprising providing an estimate of the probe area, wherein
   values in matrix M are zero outside of the estimated probe area and are 1 inside the estimated probe area, and
   K is equal to the number of 1 values in matrix M.

16. The method of claim 4 wherein determining an initial guess for a probe function comprises:
   estimating, based on the reference diffraction pattern, a power of radiation incident on a probe area of the reference target object, and
   selecting the initial guess for the probe function such that the initial guess for the probe function has an average intensity equal to the estimated average intensity.

17. The method of claim 16, wherein estimating an average intensity comprises:
   performing a fast Fourier transform on the reference diffraction pattern to produce a matrix of complex numbers, and
   summing the absolute values of the complex numbers to produce a real number, and wherein
   selecting the initial guess fur the probe function comprises:
      taking the square-root of the real number to produce a real-valued number, N,
      selecting the initial guess for the probe function P, to be P=MN/K, where
      M is a matrix representing the probe area, and K is a normalization factor.

18. The method of claim 16, further comprising providing an estimate of the probe area, wherein
   values in matrix M are zero outside of the estimated probe area and are 1 inside the estimated probe area, and
   K is equal to the number of 1 values in matrix M.

19. The method of claim 6 wherein determining an initial guess for a probe function comprises:
   estimating, based on the reference diffraction pattern, a power of radiation incident on a probe area of the reference target object, and
   selecting the initial guess for the probe function such that the initial guess for the probe function has an average intensity equal to the estimated average intensity.

20. The method of claim 19, wherein estimating an average intensity comprises:
   performing a fast Fourier transform on the reference diffraction pattern to produce a matrix of complex numbers, and
   summing the absolute values of the complex numbers to produce a real number, and wherein
   selecting the initial guess for the probe function comprises:
      taking the square-root of the real number to produce a real-valued number, N, selecting the initial guess for the probe function, P, to be P=MN/K, where
M is a matrix representing the probe area, and K is a normalization factor.

\* \* \* \* \*